United States Patent [19]

Okumura et al.

[11] 4,270,011
[45] May 26, 1981

[54] PROCESS FOR THE PRODUCTION OF TERTIARY BUTYL ALCOHOL

[75] Inventors: Yoshiharu Okumura, Kawagoe; Katsumi Kaneko, Ooi, both of Japan

[73] Assignee: Toa Nenryo Kogyo Kabushiki Kaisha, Tokyo, Japan

[21] Appl. No.: 157,689

[22] Filed: Jun. 9, 1980

[51] Int. Cl.$^3$ ............................................. C07C 29/04
[52] U.S. Cl. .................................................. 568/899
[58] Field of Search ............... 568/899, 895, 896, 897, 568/898, 900, 901

[56] References Cited

U.S. PATENT DOCUMENTS

| | | | |
|---|---|---|---|
| 3,006,970 | 10/1961 | Reuther et al. | 568/900 |
| 3,678,118 | 7/1972 | Frampton et al. | 568/896 |
| 4,096,194 | 6/1978 | Moy et al. | 568/901 |

*Primary Examiner*—Joseph E. Evans
*Attorney, Agent, or Firm*—Rebecca Yablonsky

[57] ABSTRACT

Isobutylene in a $C_4$ hydrocarbon mixture with n-butenes and butanes is selectively hydrated to tertiary butyl alcohol by carrying out the reaction with water at a temperature not above 100° C. in the presence of an acidic cation exchange resin and a sulfone.

3 Claims, No Drawings

PROCESS FOR THE PRODUCTION OF TERTIARY BUTYL ALCOHOL

BACKGROUND OF THE INVENTION

This invention relates to a process for the production of tertiary butyl alcohol (TBA) in a high yield from a $C_4$ hydrocarbon mixture containing isobutylene.

More particularly, the present invention relates to a process for the production of TBA in a high yield by selectively reacting isobutylene in a $C_4$ hydrocarbon mixture containing isobutylene with water in the presence of a porous, acid-type cation exchange resin and a sulfone.

Various processes have heretofore been proposed concerning the preparation of alcohols by hydrating corresponding olefinic unsaturated compounds in the presence of an acid-type cation exchange resin and a solvent. For example, there can be mentioned a process in which isobutylene or an isobutylene-containing hydrocarbon mixture is reacted with an aqueous solution of an organic acid in the presence of an acidic ion exchange agent as a catalyst (Japanese Patent Application OPI No. 32116/75 and Japanese Patent Publication No. 14044/78), a process in which a monohydric alcohol is added to the reaction system and the reaction is carried out by using a similar catalyst (Japanese Patent Application OPI No. 137906/75) and a process in which glycol, glycol ether or glycol diether is added to the reaction system and the reaction is similarly carried out (Japanese Patent Application OPI No. 59802/76 and U.S. Pat. No. 4,096,194).

In addition to these processes for preparing TBA by reacting water with isobutylene, there has been proposed for preparing secondary butyl alcohol (SBA) a method of reacting water with an olefinic unsaturated compound, particularly butene-1 and/or butene-2, in the presence of an acidic ion exchange resin and a sulfone at a temperature of 100° to 220° C. (Japanese Patent Application OPI No. 7605/78 equivalent to British Pat. No. 1,518,461).

These known processes for preparing TBA by hydrating isobutylene have the disadvantage of producing by-products such as addition products of isobutylene and the organic acid or organic solvent added to the reaction system, although the reaction rate is improved to some extent. Since these by-products and added solvents have a boiling point close to or lower than that of TBA, separation and recovery of TBA from these by-products and solvents are very difficult and large operating costs are necessary for recovery of TBA. Although the process for preparing SBA by reacting water with butene-1 and butene-2 at a temperature of 100° to 220° C. shows good stability of the solvent used, it is impossible to produce TBA in a high yield by selectively hydrating isobutylene because isobutylene-bearing $C_4$ hydrocarbon feed reacts with water and forms isobutylene dimer and SBA cocurrently with the formation of TBA.

SUMMARY OF THE INVENTION

Applicants have made various studies with a view to eliminating the above defects and disadvantages involved in the conventional techniques and have found that when isobutylene is caused to react with water in the presence of a specific ion exchange resin and a sulfone at a temperature not higher than 100° C., the reaction speed and conversion can be remarkably enhanced while occurence of side reactions is inhibited.

DETAILED DESCRIPTION

More specifically, in accordance with the present invention there is provided a process for preparing tertiary butyl alcohol by reacting water with isobutylene selectively from a $C_4$ hydrocarbon mixture containing isobutylene, said process being characterized in that the reaction is carried out at a temperature not higher than 100° C. in the presence of a porous acid-type cation exchange resin and a sulfone.

The composition of the isobutylene-containing $C_4$ hydrocarbon mixture used in the present invention is not particularly limited but will usually include n-butenes. Ordinarily, a mixture containing hydrocarbons having 4 carbon atoms, such as isobutylene, butene-1, butene-2, isobutane and n-butane is used, but this mixture may contain small amounts of $C_3$ or $C_5$ hydrocarbons. $C_4$ fractions containing isobutylene, obtained by steam cracking or catalytic cracking of petroleum, are preferably employed from the industrial viewpoint.

Non-cyclic and cyclic sulfones are suitably used in the present invention. For example, the following sulfones may be used.

Sulfolane of the following formula:

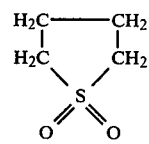

Sulfolene of the following formula:

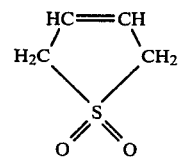

Dimethyl sulfone of the following formula:

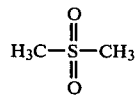

Sulfonal of the following formula:

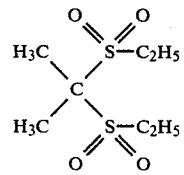

Trional of the following formula:

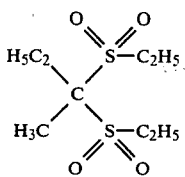

Diethyl sulfone of the following formula:

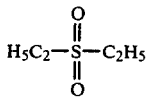

Ethylmethylsulfone of the following formula:

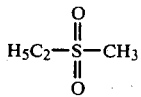

Divinylsulfone of the following formula:

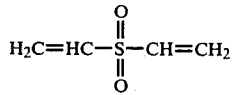

These sulfones may be used singly or in the form of a mixture of two or more of them. Ordinarily, the sulfone is used in the state dissolved in water. The amount used of the sulfone is preferably 100 to 3000 parts by weight, especially 200 to 2000 parts by weight, per 100 parts by weight of water.

A strongly acidic cation exchange resin is preferably used as the porous, acid-type cation exchange resin in the present invention. For example, there may be used a sulfonated polystyrene-type resin formed by introducing sulfonic acid groups into a styrene-divinyl benzene copolymer base, a phenol-sulfonic acid type resin formed by introducing sulfonic acid groups into a phenol-formaldehyde condensate and a perfluorosulfonic acid type resin formed by introducing sulfonic acid groups into a vinyl ether fluoride-fluorocarbon copolymer. A porous resin characterized by a surface area of at least 0.5 m$^2$/g (dry weight) and an exchange capacity of at least 2.0 meq/g (dry weight), is preferred.

The amount of the catalyst used in the suspended state differs from the amount used in a fixed bed, and in the former case it is preferred to use the catalyst in an amount of 0.1 to 10% by weight based on the aqueous solution of the solfone.

When the molar ratio of water to isobutylene is lower than 1, the conversion is lowered, and if the molar ratio of water to isobutylene is too high, the efficiency of the reaction vessel is reduced. It is preferred that the molar ratio of water to isobutylene be in the range of from 1 to 10.

The reaction is carried out at a temperature not higher than 100° C., preferably 40° to 100° C.

The reaction may be carried out under atmospheric pressure, but preferably under the vapor pressure of the starting hydrocarbon mixture at the reaction temperature or a pressure slightly higher than said vapor pressure.

The reaction may be conducted batchwise but ordinarily is conducted in a continuous manner by using a fixed bed of the porous, acid-type cation exchange resin.

The reaction time is usually 20 minutes to hours when the reaction is conducted batchwise and when conducted in a continuous manner, the liquid hourly space velocity (LHSV) of the hydrocarbon mixture is preferably from 0.3 to 10 hr$^{-1}$.

In accordance with a preferred embodiment of the present invention, the hydration reaction is carried out in the presence of a porous, acid-type cation exchange resin, e.g., a sulfonated styrene-divinyl benzene copolymer having a surface area of 0.5 to 200 m$^2$/g, especially 3 to 200 m$^2$/g, and an exchange capacity of 2.0 to 5.0 meq/g, especially 2.7 to 5.0 meq/g, and a liquid mixture of water and sulfolane, sulfolene, diethyl sulfone or dimethyl sulfone having a sulfone concentration of 50 to 97% by weight, especially 60 to 95% by weight, at a temperature of 40° to 100° C., especially 60° to 100° C., and a water/isobutylene molar ratio of from 1.0 to 10.0, preferably from 1.6 to 6.0, in a C$_4$ hydrocarbon mixture containing isobutylene, n-butenes and butanes, under a pressure sufficient to keep said C$_4$ hydrocarbon mixture in the liquid state, preferably a pressure of 7 to 18 Kg/cm$^2$.

When the sulfonated styrene-divinyl benzene copolymer is an ordinary gel-type resin having a surface area smaller than 0.1 m$^2$/g, even if the exchange capacity is higher than 2.0 meq/g, the catalytic activity is low, and when the exchange capacity is lower than 2.0 meq/g, even if the surface area is larger than 0.5 m$^2$/g, the catalytic activity is low. If the sulfone concentration is 50 to 97% by weight, the hydration reaction is promoted at a water/isobutylene molar ratio of from 1 to 10. However, even in this case, if the reaction temperature is above 100° to 200° C., dimerization of isobutylene and hydration of n-butenes are promoted and diisobutylene and SBA are formed. Accordingly, a temperature of 40° to 100° C. is effective for selective reaction of isobutylene with water.

The starting C$_4$ hydrocarbon mixture containing isobutylene is reacted with the aqueous solution of the sulfone in a catalyst packed reaction vessel, and the resulting mixture of hydration reaction products is subjected to distillation and separated into the unreacted hydrocarbon mixture and the TBA-containing aqueous solution of the sulfone. The recovered aqueous solution is subjected to distillation to separate it into crude TBA (TBA/water azeotropic mixture) and the aqueous solution of the sulfone. Water is removed from crude TBA according to customary procedures to obtain substantially pure TBA, and the separated unreacted hydrocarbon mixture and the aqueous solution of the sulfone may be recycled to the reaction vessel and used for the hydration reaction.

According to the present invention for selectively hydrating isobutylene in a C$_4$ hydrocarbon mixture containing isobutylene, the reaction rate and the conversion of isobutylene are remarkably increased and TBA can be prepared in a high yield while occurence of side reactions is inhibited. Furthermore, the boiling points of the sulfones used in the present invention are considerably higher than the boiling point of TBA. Accordingly, the sulfones can be separated very easily by distillation and can be reused without difficulty.

When the process of the present invention is utilized, isobutylene can be effectively isolated from a C$_4$ hydrocarbon mixture containing isobutylene. More specifically, according to the process of the present invention, isobutylene in a C₄ hydrocarbon mixture containing isobutylene is selectively converted to TBA, the reaction mixture is separated into the TBA-containing aqueous solution of the sulfone and the unreacted hydrocarbon mixture, TBA is isolated from the TBA-containing aqueous solution of the sulfone, and isobutylene is obtained by dehydrating TBA according to known procedures, by which high purity isobutylene can be produced.

The present invention will now be described in detail with reference to the following examples and comparative examples.

EXAMPLES 1 through 6 ene and n-butene and selectivities to TBA and SBA. The results obtained are shown in Table 1.

COMPARATIVE EXAMPLES 1 through 6

In the same reaction vessel as used in Examples 1 through 6, hydration of isobutylene was carried out in the same manner as described in Examples 1 through 6 except that the sulfone was not added, a catalyst having a surface area smaller than 0.5 m²/g or an exchange capacity lower than 2.0 meq/g was used or the reaction temperature was higher than 100° C. The reaction conditions and results obtained are shown in Table 2.

The conversions of isobutylene and n-butene and the selectivities to TBA and SBA were determined in the same manner as described in Examples 1 through 6.

TABLE 1

|  | Example 1 | Example 2 | Example 3 | Example 4 | Example 5 | Example 6 |
|---|---|---|---|---|---|---|
| Catalyst |  |  |  |  |  |  |
| surface area (m²/g) | 3 | 184 | 42 | 84 | 28 | 42 |
| exchange capacity (meq/g) | 4.3 | 3.2 | 4.7 | 4.1 | 2.7 | 4.7 |
| amount (g) | 5 | 5 | 5 | 10 | 5 | 5 |
| Solvent |  |  |  |  |  |  |
| kind | sulfolane | sulfolane | sulfolane | sulfolene | dimethyl sulfone | diethyl sulfone |
| amount (g) | 220 | 240 | 220 | 250 | 220 | 170 |
| Amount (g) of Water | 50 | 30 | 50 | 20 | 50 | 100 |
| Amount (mol) of Isobutylene | 1.0 | 1.0 | 1.0 | 0.7 | 1.0 | 1.0 |
| Reaction Temperature (°C.) | 80 | 80 | 100 | 60 | 80 | 70 |
| Reaction Pressure (Kg/cm²) | 12 | 12 | 18 | 7 | 12 | 9 |
| Reaction Time (hour) | 1 | 1 | 1 | 1 | 1 | 4 |
| Conversion (mol %) of Isobutylene | 76.0 | 82.0 | 79.0 | 86.0 | 75.0 | 90.0 |
| Conversion (mol %) of n-Butene | trace | trace | 2.0 | trace | trace | trace |
| Selectivity (mol %) to TBA | 99.0 | 99.0 | 96.0 | 100 | 99.0 | 99.0 |
| Selectivity (mol %) to SBA | — | — | — | — | — | — |

(1)The selectivity to TBA is expressed in terms of mol % of formed TBA based on reacted isobutylene.
(2)The selectivity to SBA is expressed in terms of mol % of formed SBA based on reacted n-butene.

TABLE 2

|  | Comparative Example 1 | Comparative Example 2 | Comparative Example 3 | Comparative Example 4 | Comparative Example 5 | Comparative Example 6 |
|---|---|---|---|---|---|---|
| Catalyst |  |  |  |  |  |  |
| surface area (m²/g) | <0.1 | 42 | 3 | <0.1 | <0.1 | 50 |
| exchange capacity (meq/g) | 4.8 | 4.7 | 4.2 | 4.8 | 4.8 | 0.8 |
| amount (g) | 5 | 5 | 5 | 5 | 5 | 5 |
| Solvent |  |  |  |  |  |  |
| kind | not added | not added | not added | sulfolane | sulfolane | sulfolane |
| amount (g) | 0 | 0 | 0 | 220 | 220 | 220 |
| Amount (g) of water | 270 | 270 | 270 | 50 | 50 | 50 |
| Amount (mol) of Isobutylene | 1.0 | 1.0 | 1.0 | 1.0 | 1.0 | 1.0 |
| Reaction Temperature (°C.) | 80 | 80 | 140 | 80 | 140 | 80 |
| Reaction Pressure (Kg/cm²) | 12 | 12 | 25 | 12 | 25 | 12 |
| Reaction Time (hour) | 1 | 1 | 1 | 1 | 1 | 1 |
| Conversion (mol %) of Isobutylene | 5.4 | 5.6 | 68.0 | 5.7 | 71.0 | 5.9 |
| Conversion (mol %) of n-Butene | trace | trace | 8.0 | trace | 9.0 | trace |
| Selectivity (mol %) to TBA | 85.0 | 84.0 | 43.0 | 98.0 | 45.0 | 98.0 |
| Selectivity (mol %) to SBA | — | — | 56.0 | — | 58.0 | — |

(1)The selectivity to TBA is expressed in terms of mol % of formed TBA based on reacted isobutylene
(2)The selectivity to SBA is expressed in terms of mol % of formed SBA based on reacted n-butene.

In an autoclave equipped with a stirrer, a C₄ hydrocarbon mixture containing isobutylene (40.0% of isobutylene, 40.0% of n-butenes and 20.0% of butanes) was hydrated with an aqueous solution of a sulfone in the presence of a highly porous cation exchange resin of a sulfonated styrene-divinyl benzene copolymer as a catalyst under conditions indicated in Table 1. After completion of the reaction, the reaction mixture was rapidly cooled, and the reaction product was analyzed by gas chromatography to determine conversions of isobutyl-

What is claimed is:

1. A process for the production of tertiary butyl alcohol which comprises selectively reacting isobutylene in a C₄ hydrocarbon mixture with water by carrying out the reaction at a temperature not higher than 100° C. in the presence of a porous, acid-type cation exchange resin and a sulfone.

2. A process for the production of tertiary butyl alcohol which comprises selectively hydrating isobutylene in a C₄ hydrocarbon mixture containing isobutylene, n-butenes and butanes by carrying out the reaction in the presence of a porous, acid-type cation exchange resin comprising a sulfonated styrene-divinyl benzene copolymer having a surface area of 0.5 to 200 m$^2$/g and an exchange capacity of 2 to 5 meq/g and a liquid mixture of water and a sulfone which has a sulfone concentration of 50 to 97% by weight, at a temperature of 40° to 100° C. and a water/isobutylene molar ratio in a range of 1 to 10 under a pressure sufficient to maintain said C$_4$ hydrocarbon mixture in the liquid state.

3. A process according to claim 1 or 2 wherein said sulfone is sulfolane, sulfolene, diethyl sulfone and dimethyl sulfone.

* * * * *